United States Patent
Wojtowicz

Patent Number: 5,164,109
Date of Patent: Nov. 17, 1992

[54] ALGICIDALLY ENHANCED CALCIUM HYPOCHLORITE COMPOSITIONS

[75] Inventor: John A. Wojtowicz, Cheshire, Conn.
[73] Assignee: Olin Corporation, Cheshire, Conn.
[21] Appl. No.: 531,193
[22] Filed: May 31, 1990
[51] Int. Cl.⁵ .......................... C01B 3/00; C01B 6/00; C02F 5/02; C02F 5/08
[52] U.S. Cl. .................. 252/175; 252/187.3; 252/187.28; 252/187.24; 423/474; 424/661
[58] Field of Search ............. 423/474; 424/661; 252/187.27, 187.24, 187.25, 187.28, 187.29, 187.3, 175

[56] References Cited

U.S. PATENT DOCUMENTS

| | | | |
|---|---|---|---|
| 3,440,024 | 5/1969 | Faust et al. | 423/265 |
| 3,544,267 | 12/1970 | Dychdala | 423/265 |
| 3,669,894 | 6/1972 | Faust | 252/187 |
| 3,760,064 | 9/1973 | Droste | 423/474 |
| 3,821,117 | 6/1974 | Breece et al. | 252/99 |
| 4,035,484 | 7/1977 | Faust et al. | 423/474 |
| 4,087,360 | 5/1978 | Faust et al. | 252/187.28 |
| 4,192,763 | 3/1980 | Buchan | 257/187 |
| 4,208,344 | 6/1980 | Dingwall et al. | 252/318 |
| 4,355,014 | 10/1982 | Murakami et al. | 423/474 |
| 4,780,216 | 10/1988 | Wojtowicz | 252/187.28 |
| 4,876,003 | 10/1989 | Casberg | 210/169 |
| 4,961,872 | 10/1990 | Sinclair | 252/187.24 |
| 4,973,409 | 11/1990 | Cook | 210/699 |

FOREIGN PATENT DOCUMENTS

| | | |
|---|---|---|
| 115003 | 7/1983 | Japan . |
| 760774 | 1/1977 | South Africa . |
| 803336 | 6/1980 | South Africa . |

OTHER PUBLICATIONS

Hawley's Condensed Chemical Dictionary, 11th edition Van Nostrand Reinhold, N.Y. 1987, p. 205.

Primary Examiner—Prince Willis, Jr.
Assistant Examiner—James M. Silberman
Attorney, Agent, or Firm—Allen A. Meyer, Jr.; Paul Weinstein

[57] ABSTRACT

Compositions consisting essentially of calcium hypochlorite and a water soluble zinc salt, the compositions containing from about 40 percent to about 99 percent by weight of calcium hypochlorite, provide controlled release of the components for continuous and effective sanitation and algae control to waters treated for use in swimming pools and spas.

17 Claims, 1 Drawing Sheet

ALGICIDALLY ENHANCED CALCIUM HYPOCHLORITE COMPOSITIONS

This invention relates to calcium hypochlorite compositions. More particularly, this invention relates to calcium hypochlorite compositions for use in sanitizing water.

Calcium hypochlorite is a well-known source of available chlorine for disinfecting and sanitizing water supplies such as swimming pools and spas. To sanitize water, calcium hypochlorite is added to or contacted with the water where it effectively provides the required concentrations of available chlorine In addition to providing the available chlorine levels required for the destruction of bacteria, the control of algae is a major problem in outdoor swimming pools especially in warmer climates. Algae can develop rapidly especially, for example, following a rain storm.

The separate addition of commercially available algicides to swimming pool water has been practiced but has been only partially satisfactory as the dosage level is difficult to maintain i.e. replace amounts lost by various means such as decomposition, precipitation, back washing, splashout etc.

Further, organic algicides which are commercially available such as quaternary ammonium compounds or 2-chloro-4,6-bis(ethylamino)-s-triazine (Simazine ®) have available chlorine demands which reduce the amount of available chlorine available for sanitation. Copper compounds available as algicides tend to be removed from the water fairly rapidly by precipitation and can cause staining to plaster pools. In addition, none of these commonly used swimming pool algicides are completely compatible with calcium hypochlorite when physically mixed.

Thus there is a need for a composition containing calcium hypochlorite having enhanced algicidal or algistatic properties for use in outdoor swimming pools and spas. Further, there is a need for a calcium hypochlorite composition having enhanced algicidal or algistatic properties where the algicide does not present a chlorine demand and is not removed by the filter during circulation of the pool water.

Now it has been found that the control of algae is enhanced by using a composition consisting essentially of calcium hypochlorite and a water soluble zinc salt, the composition containing from about 40 percent to about 99 percent by weight of calcium hypochlorite.

DETAILED DESCRIPTION OF THE PREFERRED EMBODIMENT

Figure 1:
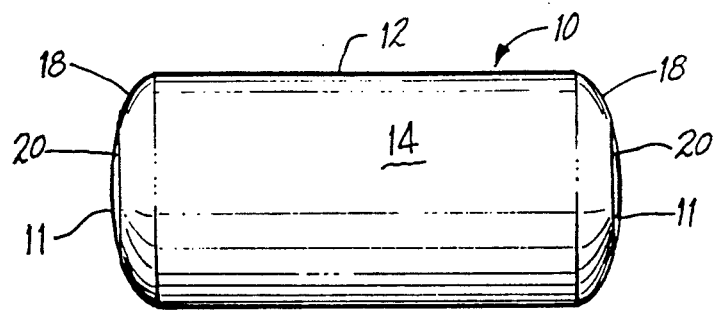
FIG. 1 is a side elevational view of a domed tablet showing an encasing shell with obliquely and inwardly tapered ends and the tablet extending out of the openings in the ends of the shell.

One component of the novel composition is calcium hypochlorite, a well-known article of commerce. Commercial neutral calcium hypochlorite compounds such as anhydrous calcium hypochlorite contain at least about 65 percent by weight of $Ca(OCl)_2$ and are quite suitable in preparing the novel compositions of the present invention. Also suitably used is "hydrated" calcium hypochlorite containing at least about 55 percent by weight of $Ca(OCl)_2$ and having a water content of from about 4 to about 15 percent. "Hydrated" calcium hypochlorite may be prepared by the methods described, for example, in U.S. Pat. No. 3,544,267, issued to G. R. Dychdala or U.S. Pat. No. 3,669,894, issued to J. P. Faust.

The second component of the novel composition is a water soluble zinc salt which includes both inorganic salts and organic salts. Examples of inorganic salts include zinc, borate, zinc bromate, zinc chlorate, zinc fluoride, zinc iodate, zinc nitrate, and zinc sulfate and hydrates thereof While zinc bromide and zinc iodide could also be used, the available chlorine would be converted to available bromine and available iodine.

Suitable organic salts include those of monocarboxylic acids containing from 1 to about 4 carbon atoms such as zinc formate, zinc acetate, or zinc propionate. Also suitable are salts of polycarboxylic acids such as zinc citrate, zinc gluconate, and zinc tartrate.

The compositions of the present invention contain calcium hypochlorite in the range of from about 40 to about 99% by weight. Preferred compositions are those having from about 60 to 97, and more preferably those having from about 50 to about 95 percent by weight of calcium hypochlorite.

The novel compositions of the present invention may contain any suitable amounts of the water soluble inorganic salt of zinc which will serve as an algicide or algistat when dissolved in pool or spa water. Suitable amounts of the composition are those which provide the water with a concentration of zinc in the range of from about 0.2 to about 10 parts per million, preferably from about 1 to about 8 parts per million, and more preferably, from about 2 to about 6 parts per million.

Where pool or spa water has been stabilized, for example, by the addition of cyanuric acid to reduce the loss of available chlorine, concentrations in the upper portion of the range may be required as algae can develop where high concentrations of the stabilizing agent are present.

The compositions also provide the water treated with available chlorine concentrations generally used for sanitizing purposes.

Surprisingly when employing the compositions of the invention in sanitizing and preventing the growth of algae, the solubilized zinc is quite stable and removal from the water for example by precipitation, occurs very slowly, in contrast to copper which tends to precipitate rather rapidly from solution.

The compositions of the present invention in granular form have good storage stability and do not evolve excessive amounts of chlorine gas should the composition become wet.

Where the compositions of the present invention are used in granular form, the prefered water soluble zinc salt is zinc sulfate and hydrates thereof.

However, to provide more accurate control of the release of the composition in the sanitizing and disinfecting of, for example, swimming pool water, compressed forms are employed which can be used in a dispersing device.

A preferred embodiment of the composition is an encased tablet, stick, etc. in which the composition is enclosed in a shell or wrapping and only portions of the composition are contacted by the water to be treated. One embodiment which can be employed as the compressed form is that described in U.S. Pat. No. 4,876,003, issued Oct. 24, 1989 to J.M. Casberg, the entire disclosure of which is incorporated by reference.

FIG. 1 shows an encased tablet, indicated generally by the numeral 10 in a side elevational view. The tablet 11 is seen extending from the shell 12 at the two opposing ends through the openings 20 in the shell 12. The shell 12 has opposing and obliquely angled end portions 18 that are sloped generally inwardly and, with reference to the top of the shell, downwardly. These ends 18 form an inwardly sloping and obliquely angled junction with the shell's elongate central section, which is indicated by the numeral 14.

Figure 2:
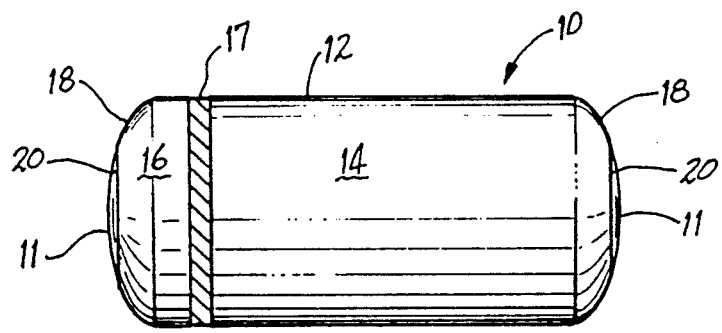
FIG. 2 is a side elevational view of an alternative embodiment of the domed tablet of FIG. 1.
Figure 3:
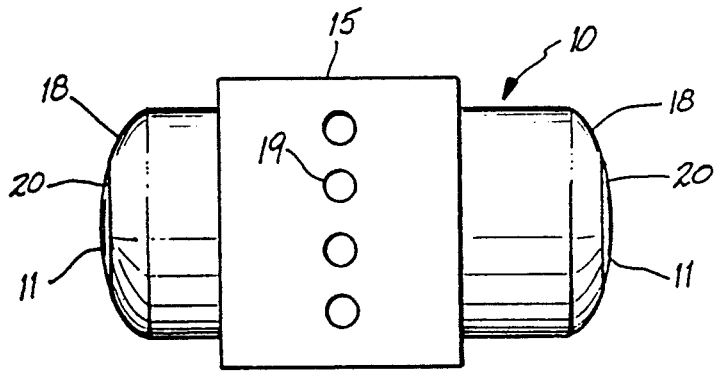
FIG. 3 is a side elevational view of an additional embodiment having an enlarged central portion and openings therein.

FIG. 2 illustrates an alternate embodiment of an encased tablet in which portion 14 containing the calcium hypochlorite is separated from portion 16 containing the water soluble zinc salt by salt barrier 17. In the alternate embodiment illustrated in FIG. 3, the water soluble zinc salt is contained in sleeve 15 having openings 19 to permit access by water to dissolve the zinc salt.

Figure 4:
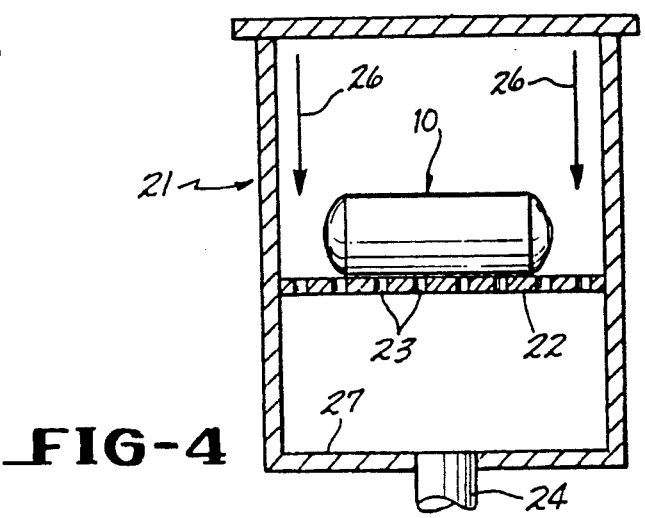
FIG. 4 is a side elevational view of the domed tablet placed on its side in a skimmer unit that is connected to a pool via a recirculation flow loop with forced water circulation.

FIG. 4 shows a skimmer unit, indicated generally by the numeral 21, that is connected in a forced water circulation system as part of a recirculation loop to a swimming pool. The top 25 is removable to permit the encased tablet 10 to be placed on the support shelf 22. Forced water circulates through the flow loop and enters the skimmer unit 21 so that it flows in a generally vertically downwardly direction indicated by the numeral 26. Water passes through the holes 23 in the support shelf 22 and continues flowing toward the bottom 27 where it exits through the skimmer outlet pipe 24 enroute to the pool.

In a segregated compressed form such as a tablet or stick any of the water soluble zinc salts identified above may be used. The calcium hypochlorite and zinc salt portions may be separated by an intermediate barrier or bridge. The bridge or barrier can be any water soluble material which is compatible with the calcium hypochlorite and the zinc salt and which dissolves readily in the water without forming a film or residue and which does not adversely alter the water chemistry. Suitable barrier materials include alkali metal chlorides such as sodium chloride or potassium chloride. The segregated compressed form is preferably encased in a shell or shrink wrapping.

Any type of a shrink wrap plastic material may be employed for use in the encasing shell. It has been found that heat shrinkable wrap such as clear, semi-rigid polyvinyl chloride has been a reliable material. A satisfactory thickness for the shrink wrap material has been about 6 mils supplied with a 75 millimeter flat dimension and a length of 11 millimeters with a minimum shrink of about 55 percent. Acceptable ranges for the shrink wrap material have been a thickness of about 5.8 to about 6.2 mils, a flat dimension of about 74 to about 76 millimeters and a length of about 108 to about 112 millimeters. The minimum shrinkage has been from about 55 to about 60 percent. A preferred size for the openings 20 in the shrink wrap material used to form the shell is about 1.0 inch diameter, with an acceptable range of about 0.09 to about 1.1 inches in diameter. Although other configurations, such as square, rectangular, pentagonal, or oval could be employed, a circular opening shape is preferred.

Additives which may be included in the novel compositions of the present invention are those, for example, which prevent scaling in pool feeders which use compressed forms of the enhanced calcium hypochlorite compositions. Suitable additives include an alkali metal salt of a phosphonobutane polycarboxylic acid represented by the formula:

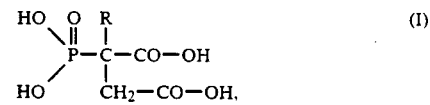

in which
R represents H or CHR'—CHR"—CO—OH,
R' represents H or CO—OH, and
R" represents H or a lower alkyl group.

The alkali metal salts of these phosphonobutane polycarboxylic acids which can be employed include sodium, potassium, lithium, and mixtures thereof, among others. Preferred as alkali metals for reasons of availability and economy are sodium and potassium, with sodium being particularly preferred.

The phosphonobutane polycarboxylic acids represented by formula (I) include phosphonobutane dicarboxylic acid, phosphonobutane tricarboxylic acid, and phosphonobutane tetracarboxylic acid which may be substituted by lower alkyl groups (R") having up to about 4 carbon atoms such as methyl, ethyl, propyl, and butyl. Of these polycarboxylic acid compounds, preferred are those in which R represents CHR'—CHR"—CO—OH and R' represents H or CO—OH, and more preferred is phosphonobutane tricarboxylic acid in which R' represents H and R" represents H.

In addition to preventing or minimizing scale formation in the dispensers, the alkali metal salt of the phosphonobutane polycarboxylic acid prevents or minimizes the precipitation of zinc due to the formation of "local areas" of concentrated solutions of calcium hypochlorite having alkaline pH's.

The calcium hypochlorite compositions of the present invention include amounts of the alkali metal salt of the phosphonobutane polycarboxylic acid of at least 0.005 percent by weight, for example, those in the range of from about 0.005 to about 5 percent by weight of calcium hypochlorite. Preferred concentrations for both operative and economic reasons are those in the range of from about 0.01 to about 3, and more preferably from about 0.1 to about 1.5 percent by weight of calcium hypochlorite.

The calcium hypochlorite compositions are prepared by admixing the calcium hypochlorite with the water soluble zinc salt and the alkali metal salt of the phosphonobutane polycarboxylic acid in any suitable manner.

The novel compositions of the present invention provide effective removal and control of algae while sanitizing and disinfecting water for outdoor swimming pools and spas.

The compositions of the present invention enhance the algicidal properties of available chlorine in pool water which has been stabilized, for example, by the addition of cyanuric acid. The water soluble zinc salts present no significant change in the available chlorine concentration.

The compositions provide controlled release of the components for continuous and effective sanitation and algae control to waters treated for use in swimming pools and spas.

In order to exemplify the process of the invention, the following examples are provided without an intent to limit the scope of the instant invention to the discussion therein. Unless otherwise indicated, all parts and percentages are by weight.

EXAMPLE 1

A 7500 gallon outdoor swimming pool having the pool water circulated at about 35 gals. perminute was maintained to provide a water analysis in the following ranges:

pH 7.2-7.8, alkalinity 80-100 ppm, hardness 300-500 ppm, and cyanuric acid 100-150 ppm. To the pool was added 330 ml. per week of mixed algae (green, black and yellow) and 180 ml. per week of a synthetic bather insult. The pool water was treated with a granular mixture containing 90% by weight of hydrated calcium hypochlorite ( 65% avail. Cl, 7% $H_2O$) and 10% by weight of zinc sulfate monohydrate to maintain the available chlorine concentration at 1 to 3 ppm with the water temperature maintained in the 80°-90° F. range. After about 190 days of operation, the zinc concentration in the pool was 6.5 ppm. During this period, the pool remained free of algae.

COMPARATIVE EXAMPLE A

A second 7500 gallon outdoor swimming pool having the pool water circulated at about 35 gals. perminute was maintained to provide a water analysis in the following ranges:

pH 7.2-7.8, alkalinity 80-100 ppm, hardness 300-500 ppm, and cyanuric acid 100-150 ppm. To the pool was added 330 ml. per week of mixed algae (green, black and yellow) and 180 ml. per week of a synthetic bather insult. The pool water was treated as needed with granular hydrated calcium hypochlorite to maintain an available chlorine concentration of 1 to 3 ppm. After only 48 days the pool had high algae counts and had developed numerous algae spots on the pool liner.

EXAMPLE 2

Stability in the Presence of Moisture

Two granular mixtures were prepared using hydrated calcium hypochlorite ( 65% avail Cl, 7% $H_2O$) and zinc sulfate monohydrate. Each mixture contained 90% by weight of hydrated calcium hypochlorite and 10% by weight of zinc sulfate monohydrate. Twenty grams of each of the mixtures were separately added to a septum vial. As a control, twenty grams of hydrated calcium hypochlorite was placed in a septum vial. To each of the vials was added 5 mls. of water. After 30 minutes, the head gas in each vial was analyzed for chlorine gas and the average for the two samples determined. The results are reported in TABLE 1.

EXAMPLES 3-4

Granular mixtures of calcium hypochlorite and zinc sulfate monohydrate were prepared containing 95% by weight of calcium hypochlorite and 5% by weight of zinc sulfate monohydrate; and 90% by weight of calcium hypochlorite and 10% by weight of zinc sulfate monohydrate. The particle size of the calcium hypochlorite was −20/+30 mesh and that of the zinc sulfate was −70/+80 mesh. Each mixture (20 grams) was added to three septum vials. As a control, 20 g of the calcium hypochlorite without zinc sulfate was added to three septum vials. The vials were placed in an oven maintained at 45° C. Individual vials were withdrawn at 10, 20, and 30-day intervals and analyzed for head gas composition by gas chromatography and the available chlorine content of the calcium hypochlorite determined after separation from zinc sulfate. The data, tabulated in Table I, show zinc sulfate had essentially no effect on the stability of calcium hypochlorite.

TABLE I

REACTIVITY/STABILITY TESTS ON HTH-ZnSO4.H2O GRANULAR MIXTURE

| | | Reactivity With 20% H2O % Cl2 | Stability @ 45 C | | | | | |
|---|---|---|---|---|---|---|---|---|
| | | | Net Av. Cl Loss (%) | | | Gassing: % Cl2 | | |
| | ZnSO4.H2O (%) | | 10 | 20 | 30 | 10 | 20 | 30 days |
| Control | 0 | 0.1 | | | | | | |
| Example 2 | 10 | 0.8 | | | | | | |
| Control | 0 | | 3.6 | 9.2 | 13.3 | 0 | 1.1 | 27.8 |
| Example 3 | 5 | | 3.7 | 7.8 | 13.2 | 0 | 1.1 | 29.2 |
| Example 4 | 10 | | 6.5 | 9.5 | 13.8 | 0 | 0.7 | 26.5 |

What is claimed is:

1. A composition consisting essentially of from about 40 percent to about 99 percent by weight of calcium hypochlorite, an algae controlling amount of a water soluble zinc salt, and an effective amount to inhibit scale formation of an alkali metal salt of a phosphonobutane polycarboxylic acid represented by the formula:

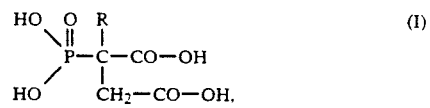

in which
R represents H or CHR'—CHR"—CO—OH,
R' represents H or CO—OH, and
R" represents H or a lower alkyl group.

2. The composition of claim 1 in which the water soluble zinc salt is an inorganic salt selected from the group consisting of zinc, borate, zinc bromate, zinc chlorate, zinc fluoride, zinc iodate, zinc nitrate, and zinc sulfate and hydrates thereof.

3. The composition of claim 1 in which the water soluble zinc salt is a zinc salt of a monocarboxylic acid having from 1 to about 4 carbon atoms.

4. The composition of claim 1 in which the water soluble zinc salt is a zinc salt of a polycarboxylic acid selected from the group consisting of zinc citrate, zinc gluconate, and zinc tartrate.

5. The composition of claim 1 in which the amount of alkali metal salt of a phosphonobutane polycarboxylic acid is in the range of from about 0.005 to about 5 percent by weight of calcium hypochlorite.

6. The composition of claim 2 in which the water soluble zinc salt is zinc sulfate and hydrates thereof.

7. The composition of claim 6 which contains from about 60 percent to about 97 percent by weight of calcium hypochlorite.

8. The composition of claim 7 in granular form.

9. A segregated compressed form consisting essentially of from about 40 percent to about 99 percent by weight of calcium hypochlorite, an algae controlling amount of a water soluble zinc salt, and an effective amount to inhibit scale formation of an alkali metal salt of a phosphonobutane polycarboxylic acid represented by the formula:

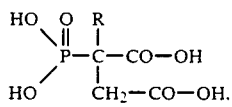 (I)

in which
R represents H or CHR'—CHR"—CO—OH,
R' represents H or CO—OH, and
R" represents H or a lower alkyl group.

10. The segregated compressed form of claim 9 in which the water soluble zinc salt is an inorganic salt selected from the group consisting of zinc borate, zinc bromate, zinc chlorate, zinc fluoride, zinc iodate, zinc nitrate, and zinc sulfate and hydrates thereof.

11. The segregated compressed form of claim 9 in which the water soluble zinc salt is a zinc salt of a monocarboxylic acid having from 1 to about 4 carbon atoms.

12. The segregated compressed form of claim 9 in which the water soluble zinc salt is a zinc salt of a polycarboxylic acid selected from the group consisting of zinc citrate, zinc gluconate, and zinc tartrate.

13. The segregated compressed form of claim 10 in which the amount of alkali metal salt of a phosphonobutane polycarboxylic acid is in the range of from about 0.005 to about 5 percent by weight of calcium hypochlorite.

14. The segregated compressed form of claim 9 in which a bridge separates the calcium hypochlorite portion and the zinc salt portion.

15. The segregated compressed form of claim 14 in which the bridge is an alkali metal chloride.

16. The segregated compressed form of claim 15 in which the water soluble zinc salt is zinc sulfate and hydrates thereof.

17. The segregated compressed form of claim 15 which contains from about 60 percent to about 97 percent by weight of calcium hypochlorite.

* * * * *